United States Patent [19]

Bramson

[11] 4,308,230
[45] Dec. 29, 1981

[54] BLOOD OXYGENATOR

[76] Inventor: Mogens L. Bramson, 35 - 21st Ave., San Francisco, Calif. 94121

[21] Appl. No.: 42,923

[22] Filed: May 29, 1979

Related U.S. Application Data

[62] Division of Ser. No. 744,675, Mar. 7, 1977, Pat. No. 4,168,293.

[51] Int. Cl.³ .............................................. A61M 1/03
[52] U.S. Cl. .................................. 422/48; 128/DIG. 3; 422/46
[58] Field of Search .............................. 261/DIG. 28; 128/DIG. 3; 422/46, 48

[56] References Cited

U.S. PATENT DOCUMENTS

| | | | |
|---|---|---|---|
| 3,034,505 | 5/1962 | Sobol | 128/DIG. 3 U X |
| 3,219,573 | 11/1965 | Chen et al. | 210/231 X |
| 3,332,746 | 7/1967 | Claff et al. | 422/48 X |
| 3,413,095 | 11/1968 | Bramson | 422/48 X |
| 3,484,211 | 12/1969 | Mon et al. | 422/48 X |
| 3,534,060 | 10/1970 | Dibelius et al. | 422/48 X |
| 3,540,595 | 11/1970 | Edwards | 422/48 X |
| 3,834,544 | 9/1970 | Tyson et al. | 422/48 X |
| 3,839,204 | 10/1974 | Ingenito et al. | 422/48 X |
| 3,979,297 | 9/1976 | Bardon et al. | 210/232 |
| 3,979,298 | 9/1976 | Breysse et al. | 210/232 |
| 3,980,564 | 9/1976 | Barden et al. | 210/433 M X |
| 3,996,141 | 12/1976 | Updike | 210/501 |

*Primary Examiner*—Barry Richman
*Attorney, Agent, or Firm*—Edward B. Gregg

[57] ABSTRACT

Blood units and water units for membrane type blood oxygenator in which blood units are separated from water units by oxygen units; oxygen diffuses through membranes of blood units from oxygen units and water units apply pressure to blood units through intervening oxygen units. The blood unit is formed by a frame having a pair of opposing sides and a pair of opposing ends, the ends being imperforate, the sides being formed with flow-through passages for flow of blood from one blood unit to the next and with lateral passages for flow of a portion of the blood into, through and out of the blood unit, three being a semi-permeable membrane affixed to opposite faces of the frame. The water unit comprises a water impermeable, expansible water mattress having rigid end members formed with water flow-through passages for flow of water from one water unit to the next and having lateral passages for flow of a portion of the water into, through and out of the mattress.

3 Claims, 22 Drawing Figures

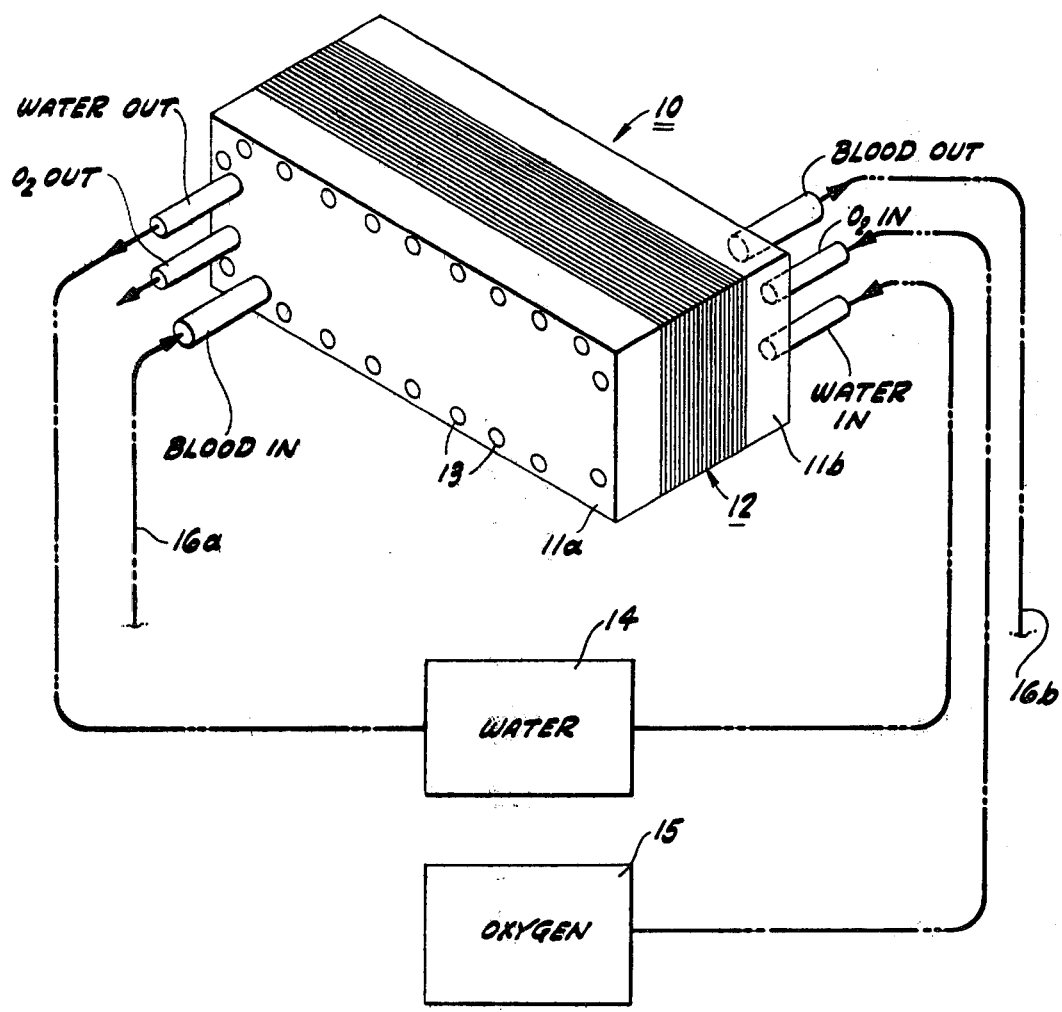

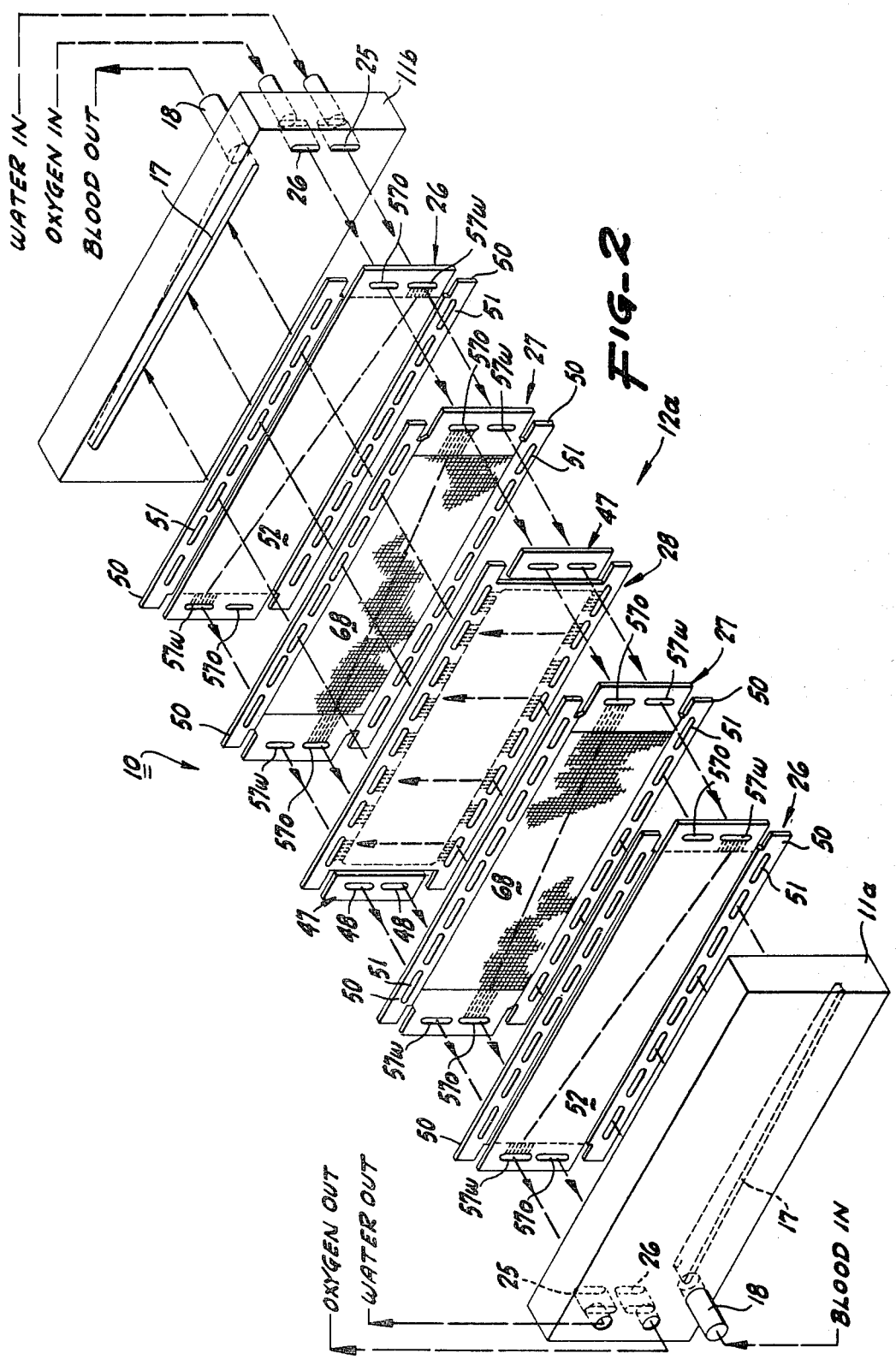

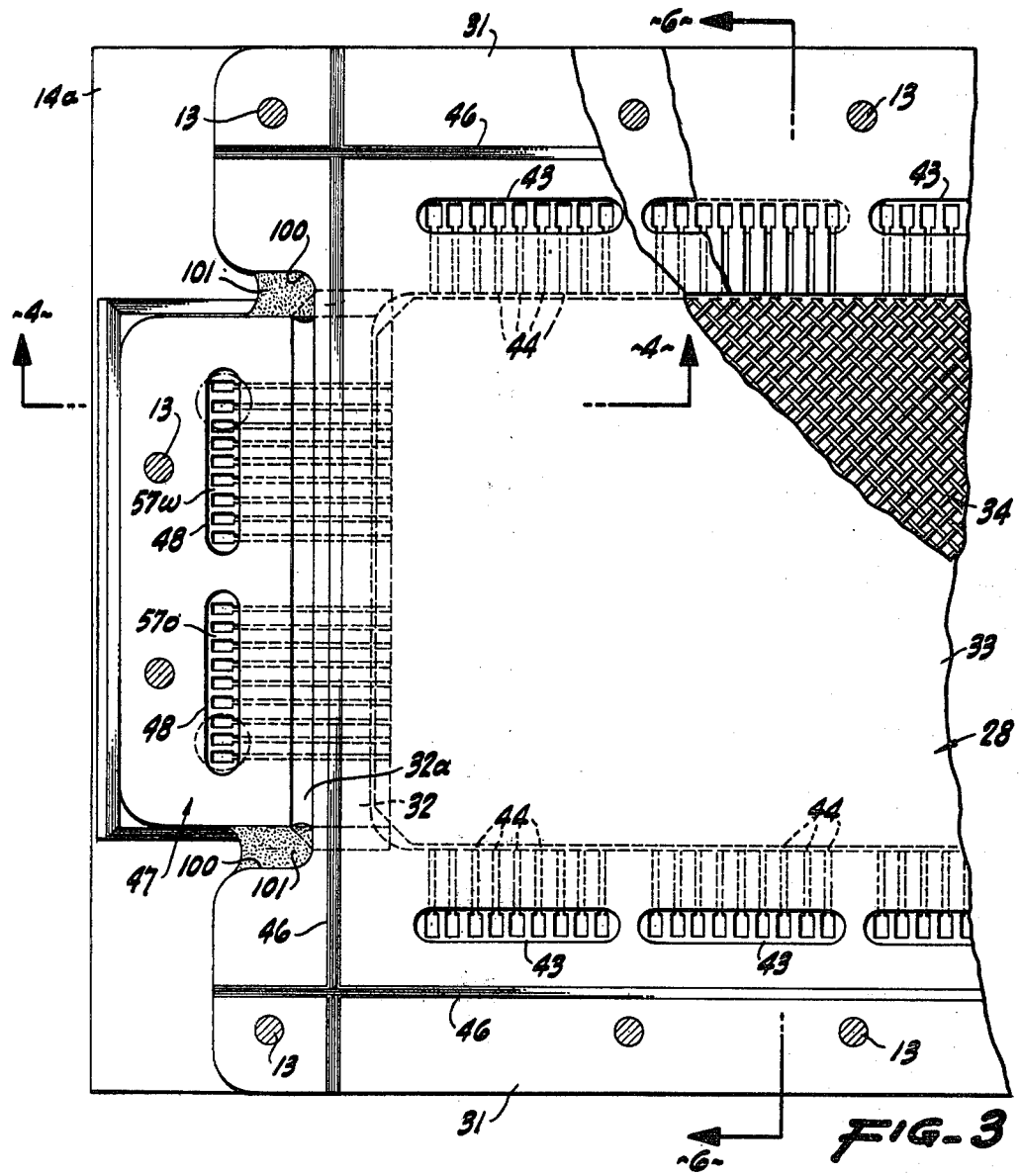
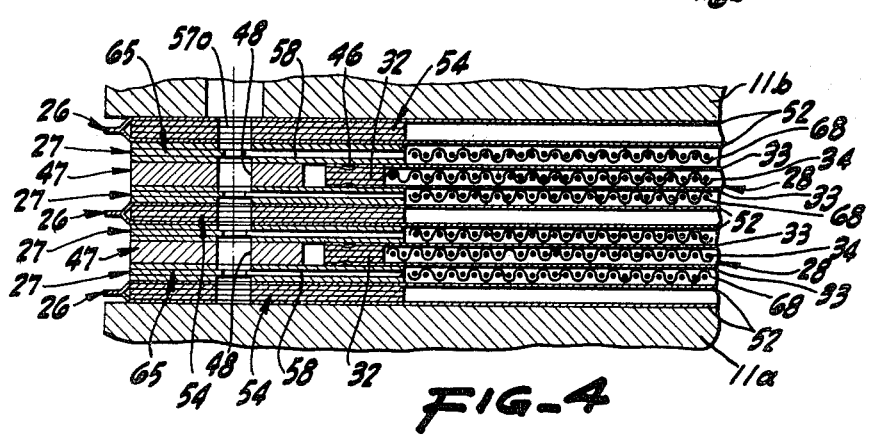

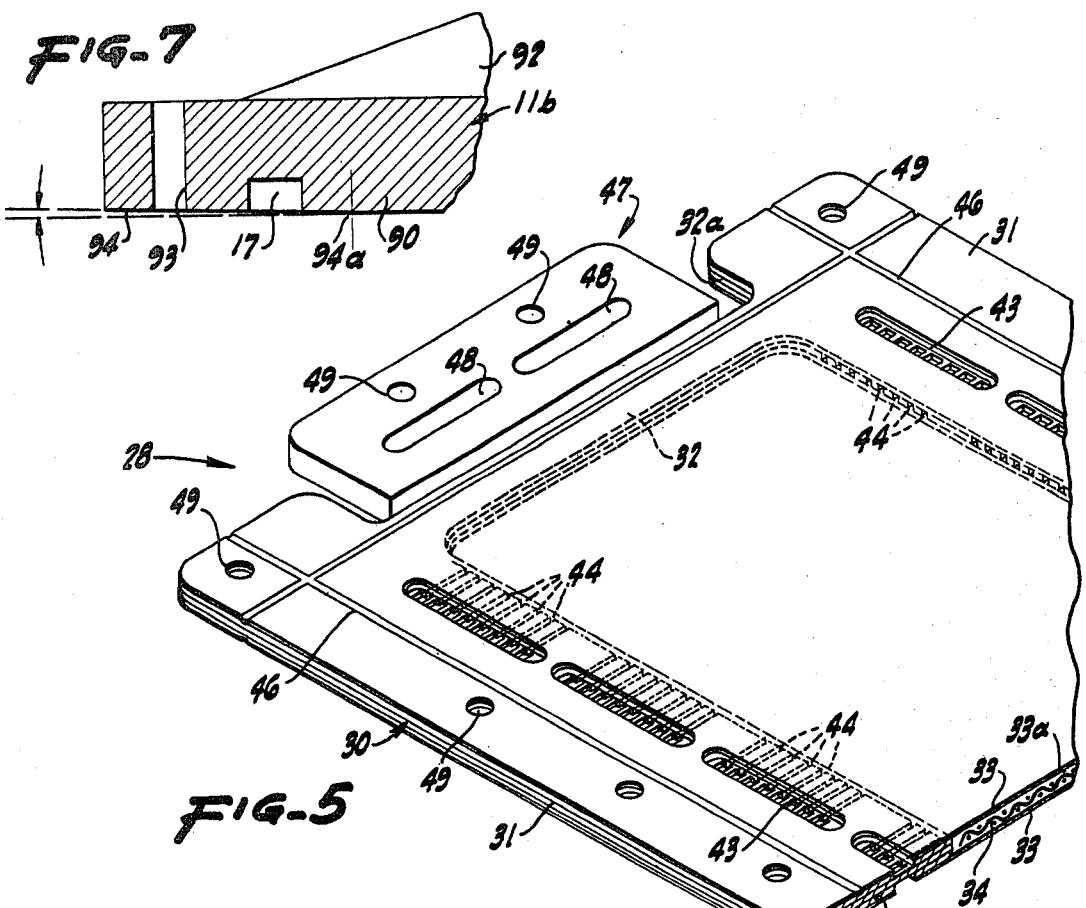

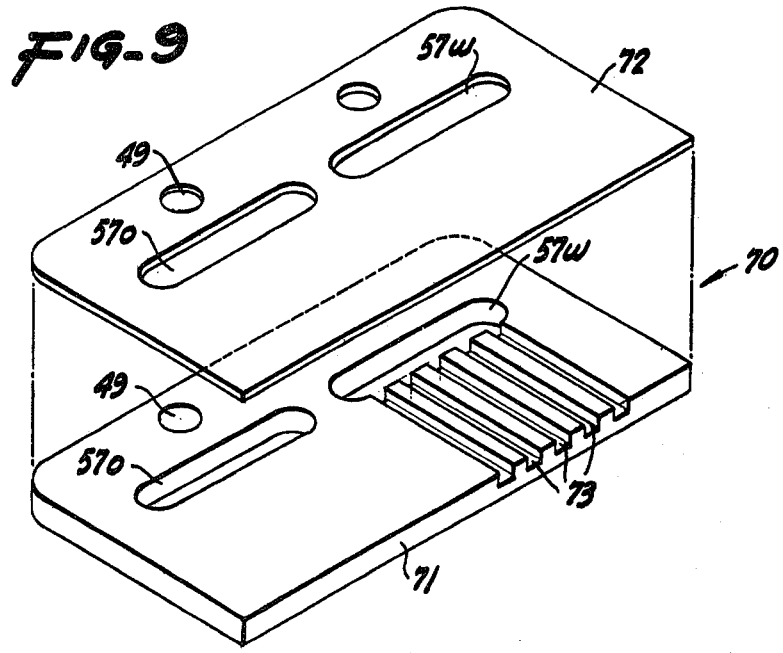
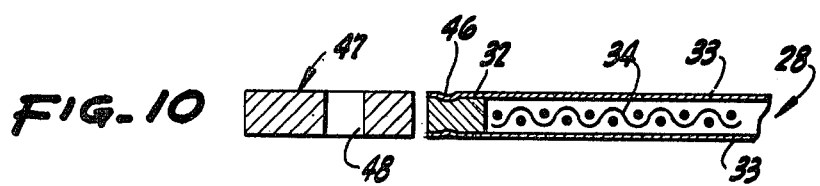
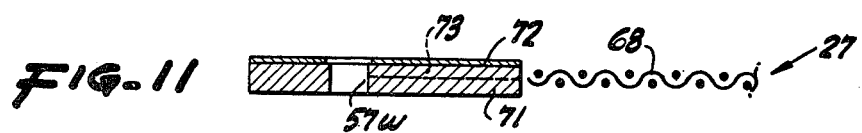
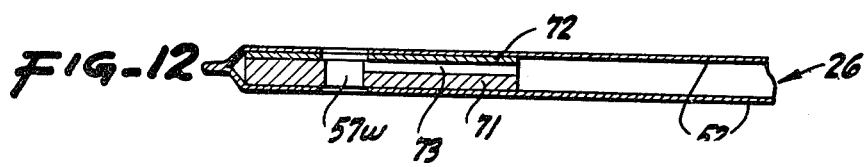
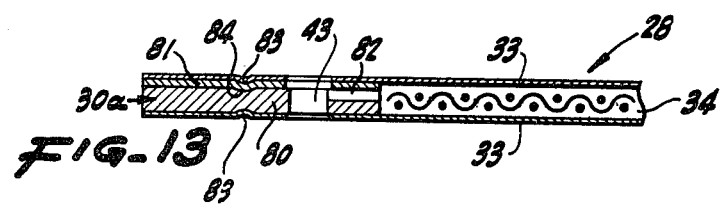

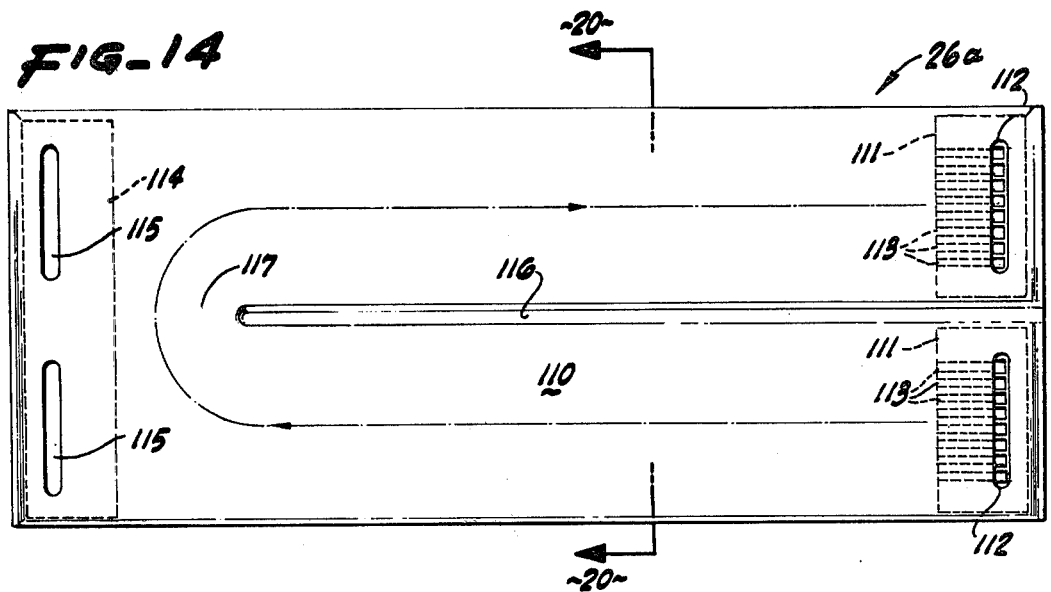
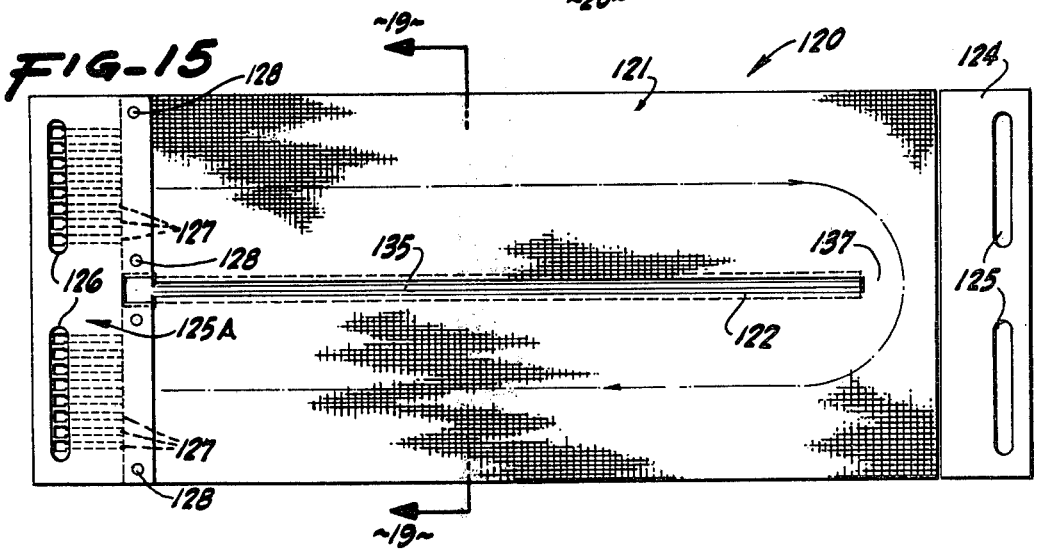
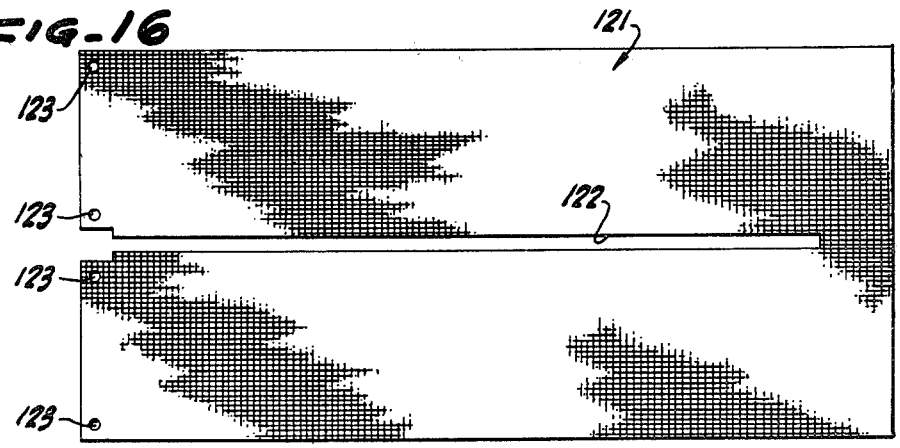

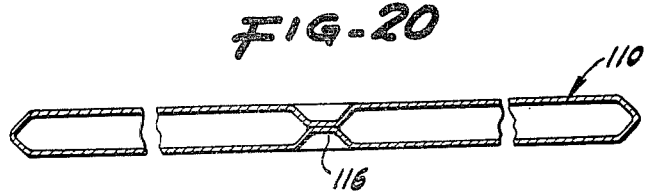
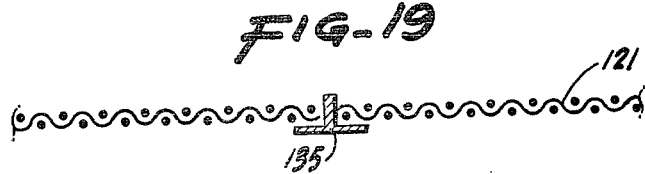
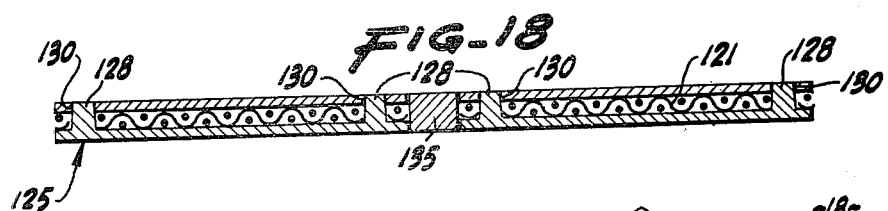
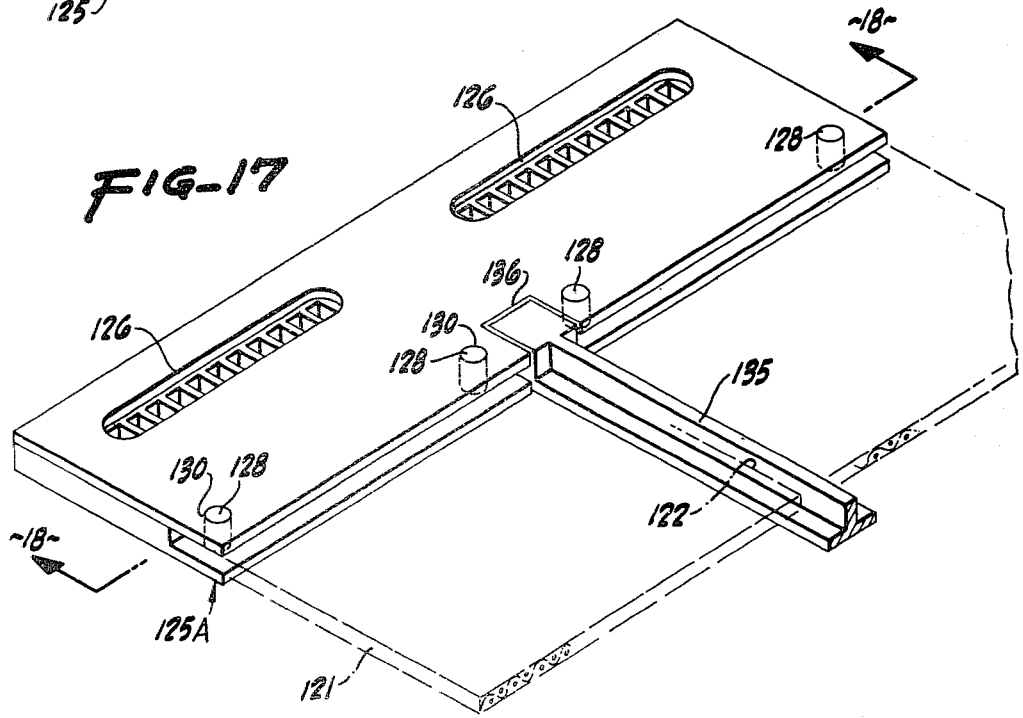

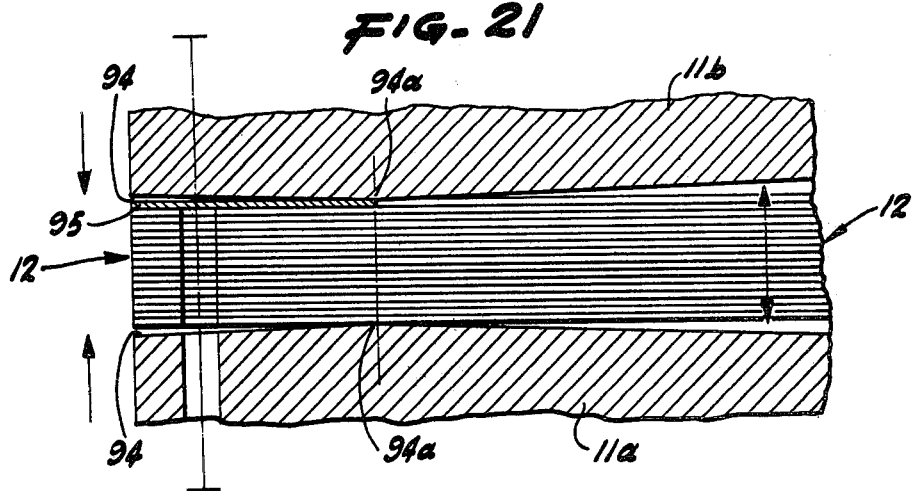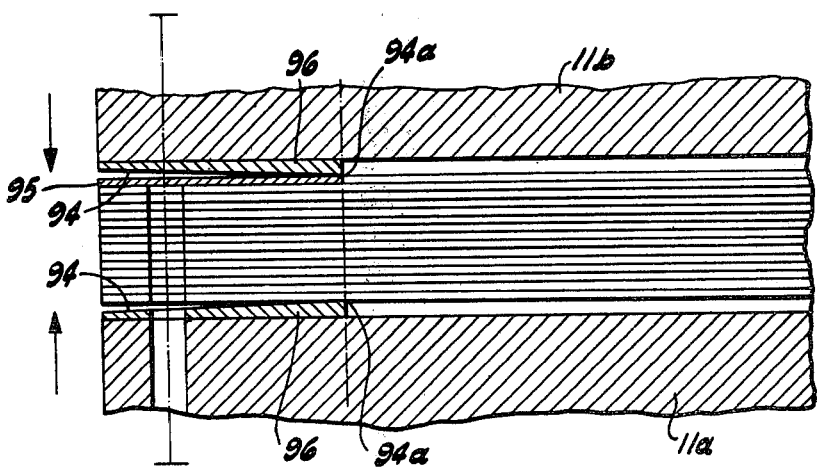

BLOOD OXYGENATOR

This application is a division of my copending application, Ser. No. 774,675, filed Mar. 7, 1977 now U.S. Pat. No. 4,168,293 issued Sept. 18, 1979.

This invention relates to blood oxygenators of the membrane type wherein a semi-permeable membrane (as defined above) separates the blood from the oxygen, oxygen passes through the membrane into the blood and carbon dioxide passes from the blood through the membrane into the stream of oxygen. When an aqueous solution of hydrogen peroxide is used instead of oxygen gas the hydrogen peroxide diffuses into the membrane and is broken down into oxygen and water by a catalyst and the oxygen passes into the blood.

Blood oxygenators used during open heart surgery to take over the function of the natural lungs are of several types, including the bubble type in which the oxygen is bubbled through the blood in direct contact therewith, and the membrane type identified in the preceding paragraph and in the Abstract of Disclosure.

Bubble type oxygenators are simpler and for that reason are widely used, but the trend is toward the membrane type of oxygenator. The latter functions more nearly like the natural lung in that it separates the stream of oxygen from the blood and allows communication between the oxygen and the blood only by diffusion through a semi-permeable membrane. There is evidence that this more nearly natural functioning of membrane oxygenators is less harmful to the blood than the functioning of bubble type oxygenators, especially during the course of lengthy (for example, five hours and more) open heart surgery.

However, membrane oxygenators heretofore have been much more complex than bubble oxygenators, so that as a practical matter they must be taken apart, cleaned, sterilized and reassembled with new membranes after each use. This is an expensive, time-consuming and cumbersome operation. One such oxygenator is that described in my U.S. Pat. No. 3,413,095, which has been very successful in use but suffers from the nondisposable characteristic described above.

In Bramson and Tyson U.S. Pat. No. 3,834,544 there is described a membrane type blood oxygenator which is intended to be of the disposable type, that is to say, sufficiently inexpensive to manufacture so that it can be used once and discarded. However, to date that oxygenator has not been proved to be practicable in use, one of its defects being that it offers the possibility of inadvertent leakage of water from the water circuit into the blood circuit. Water leaking into the blood causes hemolysis and dilution and is harmful to the patient. Added to this drawback is the fact that inadvertent leakage of water from the water circuit into the blood circuit of a membrane oxygenator is not likely to become evident at once. This presents the possibility of long continued, harmful leakage of water into the blood circuit before the leakage is ascertained.

A further disadvantage of the membrane oxygenator of U.S. Pat. No. 3,834,544 is the fact that to make and keep all fluid compartments leak-proof, it is necessary to employ cumbersome clamps to overcome structural problems which are described hereinbelow.

It is an object of the present invention to provide improved, disposable membrane-type blood oxygenators.

It is a further object of the invention to provide disposable membrane-type blood oxygenators of simplified construction, such that it is economically feasible to employ the oxygenator once and once only and then discard it, such oxygenator being free of defects such as the possibility of leakage of water from the water circuit into the blood circuit, and/or such that control over critical dimensions such as the thickness mentioned above is readily accomplished without inconvenience.

It is a further and particular object of the present invention to provide a blood unit including a blood compartment, such unit having inlet and outlet passages for the blood, the blood unit being so isolated from water units used with it that leakage of water into the blood units is precluded.

The above and other objects of the invention will be apparent from the ensuing description and the appended claims.

Certain embodiments of the invention are illustrated by way of example in the accompanying drawings, in which:

FIG. 1 is a perspective view of the apparatus of the invention shown diagrammatically in its entirety and connected to sources of water and oxygen and to the circulatory system of a patient undergoing open heart surgery;

FIG. 2 is a largely diagrammatic, exploded perspective view showing the end plates in simplified form and showing a single blood unit, two oxygen units and two water units. In this figure for the sake of simplicity certain components of adjacent water and oxygen units are shown as separate components whereas in actual practice (and as will be apparent from the description below) such components are common to both a water unit and an oxygen unit. Further, whereas in practice a number of blood units and an appropriately larger number of oxygen and water units will be employed, for simplicity only one blood unit, two oxygen units and two water units are shown.

FIG. 3 is a plan view broken away to reveal portions of a blood unit, a water unit and an oxygen unit;

FIG. 4 is a section taken along the line 4—4 of FIG. 3;

FIG. 5 is a fragmentary perspective view of a blood unit;

FIG. 6 is a section taken along the line 6—6 of FIG. 3. In this figure the end plates (which are shown for simplicity as simple blocks in FIGS. 1 and 2) are shown in reinforced form;

FIG. 7 is a fragmentary sectional view of one of the end plates showing a chamfer along an edge which serves a useful purpose as described hereinbelow;

FIG. 9 is a perspective view showing an alternative and preferred form of end insert for the water units, such being also used for the oxygen units;

FIG. 10 is a fragmentary longitudinal section through a blood unit;

FIG. 11 is a fragmentary longitudinal section through an oxygen unit;

FIG. 12 is a fragmentary longitudinal view through a water unit;

FIG. 13 is a fragmentary transverse sectional view through a blood unit;

FIG. 14 is a plan view of an alternative form of water unit;

FIG. 15 is a plan view of an alternative form of oxygen unit;

FIG. 16 is a plan view of the screen for the oxygen unit of FIG. 15;

FIG. 17 is a perspective view of the oxygen unit of FIG. 15;

FIG. 18 is a section along the line 18—18 of FIG. 17;

FIG. 19 is a section along the line 19—19 of FIG. 15;

FIG. 20 is a section along the line 20—20 of FIG. 14;

FIG. 21 is a view similar to FIG. 7 but on a larger scale and showing more clearly the forces acting on the end plates and the stack of blood, oxygen and water units held together by the end plates; and FIG. 22 is a view similar to FIG. 7 showing an alternative way of forming a chamfer.

Figure 8:
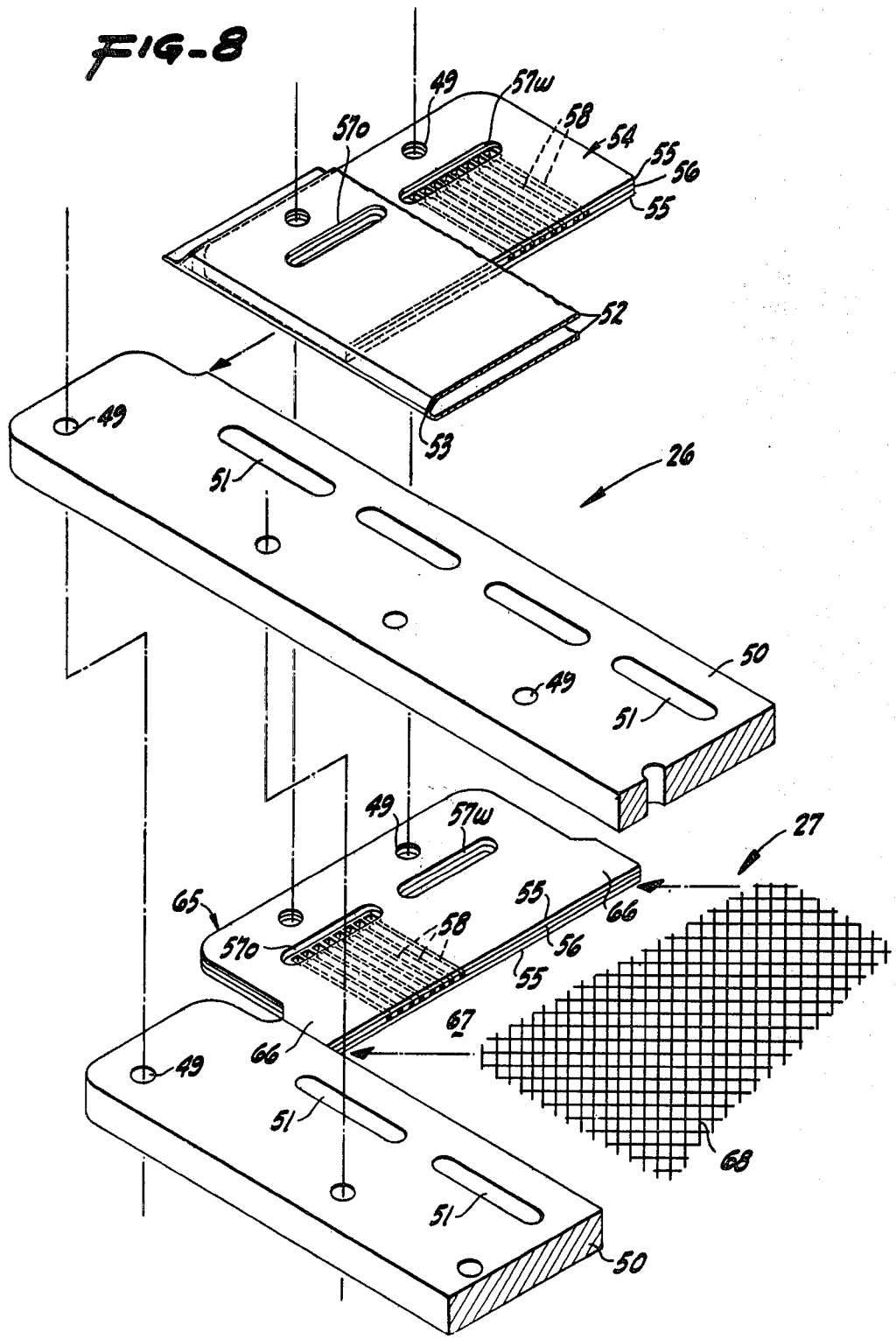
FIG. 8 is a fragmentary, exploded perspective view showing a water unit and an oxygen unit. In this figure a single component common to the water unit and the oxygen unit is shown, for clarity, as two separate components.

Referring now to the drawings, and first to FIG. 1, the device or apparatus of the present invention is generally designated by the reference numeral 10 and it is shown as comprising end plates 11a and 11b between which is an assembly or stack of water, oxygen and blood units collectively designated by the reference numeral 12, the whole assembly being held together by bolts 13 which pass through the end plates 11a and 11b and through the assembly 12.

The device or apparatus 10, i.e., the apparatus of the present invention, is shown connected to certain external equipment which may be of well known design. For example, water and oxygen circulating and/or supply means are shown at 14 and 15, respectively, and they are shown only diagrammatically. The water supply 14 will include a pump and thermostatic means to effect circulation of the water and to maintain proper water and blood temperature and it may include a source of nitrogen under pressure to pressurize the water circuit. The oxygen supply 15 will comprise a source of oxygen under pressure and suitable valving means, pressure gauge and flow gauge. Blood inlet line 16a and outlet line 16b will be connected to the venous line and the arterial line from and to the patient, respectively, by suitable means which are well known in the art, and which include a pump in the venous line. Bramson U.S. Pat. No. 3,413,095 describes suitable equipment of this type.

Referring now to FIG. 2, the end plate 11a is formed on its inner surface with a long horizontal blood flow slot or manifold 17 connected at one end to a blood inlet 18. End plate 11a is also formed with short vertical slots 25 and 26 for water and oxygen outlets, respectively. End plate 11b is similarly formed but is inverted. In FIGS. 1 and 2, end plates 11a and 11b are shown, for simplicity, as simple blocks but, preferably, they are constructed in another manner, for example as shown in FIGS. 6 and 7, and as described hereinbelow. Between the end plates 11a and 11b a simplified assembly or stack 12a is shown consisting of (reading from left to right) a water unit 26, an oxygen unit 27, a single blood unit 28, another oxygen unit 27 and another water unit 26. This simplified drawing serves the purpose of illustrating the flow of fluids (blood, water and oxygen) through the apparatus. In actual practice, the assembly 12 will usually consist of a number of blood units sufficient to provide a total membrane surface adequate for oxygenating the patient's blood. In practice, a typical adult size preferred assembly 12 would have the following stacking order, using the symbols W to indicate a water unit, O to indicate an oxygen unit and B to indicate a blood unit:

W—O—B—O—B—O—W—O—B—O—B—O—
W—O—B—O—B—O—W—O—B—O—B—O—
W—O—B—O—B—O—W—O—B—O—B—O—W—

The assembly illustrated above has the advantage of using fewer water units W (one for each two blood units) and it therefore results in a more compact assembly of units, yet is sufficient to hold the thickness of the blood units (hence the depth of the blood path in the blood units) constant and equal to the thickness of the blood screens described below. However, for purposes of more adequate temperature control of the blood, a greater number of water units may be employed, for example, one water unit W for each blood unit B, thus W—O—B—O—W—O—B—O—W—. That is, the module is —W—O—B—O—.

Referring now to FIG. 5, a blood unit 28 is there shown. It comprises a rectangular blood frame 30 including side members 31 and recessed end members 32 forming, with the side members, a recessed area 32a. This frame 30 is overlaid by a pair of membranes 33 which are permeable to gas (oxygen and carbon dioxide) but impermeable to liquid (blood and water). Within the cell or blood space 33a formed by the membranes 33 is a screen 34. Typical and preferred materials and characteristics of the membranes 33 and the screen 34 are as follows: For the membrane, microporous polypropylene or microporous Teflon may be used. Also, silicon rubber or Teflon material in which the gases dissolve and diffuse. The screen 34 may be woven or extruded from polypropylene or polyester and may have a mesh of 18 to 22 counts per inch and a thickness (which determines the depth of blood cavity 33a) of 0.020 inch.

The blood frame 30 is shown in three parts consisting of top and bottom parts (as viewed in FIG. 5) 40 and 41 and an inner part 42. Each of these parts is formed with longitudinal blood flow-through slots 43 along the side portions 31 and the inner part 42 is also formed with a series of transverse slots 44 extending from the respective slots 43 to the inner edge, and therefore to the blood space 33a. The flow-through slots 43 are in registry with one another to permit flow of blood through the assembly 12 (FIG. 1), as well as out into the blood space, as will be described hereinafter. The frame members 40, 41 and 42 may be constructed of any suitable material having appropriate structural characteristics for the purpose and also to be compatible with the fluids flowing in the system and capable of heat sealing with the membrane. A suitable material is polypropylene. The membranes 33 are heat sealed at 46 to the frame along side members 31 and end members 32, thus forming a membrane envelope. As will be seen, end members (of which only one is shown in FIG. 5, there being another one at the other end) are imperforate.

A spacer member 47 is received in the recess 32a at each end of the blood frame and it is formed with a pair of flow through slots 48 extending therethrough, which are intended for the flow of oxygen and water as described hereinafter. As will be seen, the side parts 31 of the frame 30 and the insert 47 are provided with bolt holes 49, those in the side members 31 being outside the blood flow-through slots 43 and those in the insert or spacer 47 lying outside the oxygen and water flow through slots 48.

Referring now to FIG. 8, a water unit 26 and an oxygen unit 27 are shown. This assembly or pair of an oxygen unit and a water unit have a single side frame member 50 on each long side, which is common to both the water unit 26 and the oxygen unit 27. However, as explained above, the side member 50 is shown twice to show its relation to the water and oxygen units. As will be apparent, the water and oxygen units may, at particular places in the assembly 12 by W—O, or O—W—O, or O alone (i.e., not adjacent a water unit). The thickness of the side member 50 will vary accordingly. That is, the side piece for a W—O pair will be equal to the thickness of an adjacent pair of water and oxygen units; the side pieces for an O—W—O triplet will be equal to the thickness of two oxygen units and one water unit; and the thickness of a side piece for a single oxygen unit will be equal to the thickness of an oxygen unit. The side members 50 are formed with blood flow-through slots 51 which register with slots 43 in the side members of the blood units.

A water envelope or mattress 52 is provided which is of water and gas-impermeable material, for example, flexible polyvinyl chloride, polypropylene, polyethylene or polyvinyl alcohol. This material is sealed along all edges at 53, that is to say, two sheets of the material are seamed together as by heat sealing, vulcanizing or other suitable means. Instead of being formed from separate sheets and heat sealed, the water mattress may be formed from a seamless tube and heat sealed at the ends. In either case before the ends are sealed, the water mattress is fitted at each end with an insert 54 which, in the embodiment shown in FIG. 8, is in three parts consisting of upper and lower parts 55 ("upper" and "lower" being used with reference to FIG. 8, it being understood that in use the water, oxygen and blood units will be on edge) and a third or inner part 56. All of these components are slotted at 57-W (water flow-through slots) and 57-O (oxygen flow-through slots), the water and oxygen slots registering with one another and providing water and oxygen flow-through passages, respectively. The water mattress is similarly slotted. The inner part 56 is also formed with a series of slots 58 which extend from the water flow-through slot 57-W inwardly to the edge of the insert, thereby communicating the slot 57-W with the interior of the water mattress. The oxygen flow-through slot 57-O in part 56 is free of such transverse slots.

Each end of the water mattress is fitted with such an insert, the two inserts being identical to one another but being inverted in relation to one another such that flow of water through the water mattress is diagonal, as indicated in FIG. 2. Diagonal flow is advantageous because it minimizes channeling and enhances uniform water flow through the mattress.

Each end of an oxygen unit 27 is provided with an end member or insert 65 having projecting ears 66 which abut the side frame member 50 and which, together with the frame members forms an oxygen space 67 within which there is a screen 68. Materials and characteristics suitable for this screen are as follows:

Polypropylene or polyethylene may be used or any of a number of weavable or extrudable plastic materials may be used. Overall thickness of the screen may be from 0.015 to 0.045 inch. Mesh of the weave may be 10 to 25 counts per inch.

Except for the configuration of its perimeter, the insert 65 is identical with the insert 54 described above with reference to the water unit. Similar parts are similarly numbered. The inner member 56 is formed with transverse slots 58 as in the case of the insert 54, but these slots connect with the oxygen flow through slots 57-O rather than the water flow through slots 57-W. As in the case of the inserts 54 of the water unit, the insert 65 at one end of an oxygen unit is inverted in relation to the insert 65 at the other end, whereby the flow of oxygen through the oxygen unit is diagonal and uniform flow is enhanced.

Referring now to FIG. 9, an alternative and preferred two-piece construction for the insert 54 is shown and it is generally designated by the reference numeral 70. It will be understood that although this depicts an insert for a water unit 26, the same construction may be employed for the end inserts 65 of an oxygen unit, with due allowance for the ears 66.

As shown in FIG. 9, the insert 70 consists of a bottom (as viewed in FIG. 9) piece 71 formed with transverse grooves 73 communicating with the water slot 57-W and a top or cover piece 72. As in the case of the inserts 54 and 65, bolt holes 49 are provided which lie outside of the slots 57-O and 57-W.

A similar simplified construction may be employed for the blood frame 30, such being shown in FIG. 13 in transverse section, and in FIG. 10 in longitudinal section.

Referring to FIG. 13, the blood side frame member is generally designated by the reference numeral 30a and it comprises a lower (as shown in FIG. 13) thick strip or plate 80 and a thinner cover plate 81. The lower member 80 is formed with a series of grooves, one such groove being shown at 82 and serving to provide blood flow from the blood flow-through slot 43. That is to say, in this construction the side frame members 30a are formed with grooves molded in the lower portion 80 rather than having a third, comb-like component such as shown at 42 at FIG. 5. Also shown in FIG. 13 are heat seals 83 between the membranes 33 and the frame members, and also a heat seal 84 between the top frame member 81 and the bottom frame member 80. Such heat seals extend around the entire perimeter of the blood frame 30a.

From the description above, and with particular reference to FIG. 2 (which, as stated, is a simplified arrangement of blood, oxygen and water units, but which will suffice for the purpose of illustrating the flow of fluids) it will be apparent that the flow paths of the three fluids (blood, water and oxygen) are as follows: Blood fills the groove or manifold 17 in end plate 11a and flows through blood flow-through slots 51 in the adjacent water unit 26 and oxygen unit 27. (As explained above, a single side member 50 bridges a pair of water and oxygen units, but for simplicity, each unit is shown with a separate side member 50). At the level of the blood unit 28 a portion of this stream of blood flows through slots 44 (see FIG. 5), or through grooves 82 if the construction of FIG. 13 is used, into the respective blood space 33a, thence across the blood envelope to slots 44 (or grooves 82) on the opposite sides and then through the blood flow-through slots 51 to groove 17 in end plate 11b and out of the apparatus, to the artificial system of the patient. It will be understood that in actual practice where multiple blood units are employed rather than a single blood unit as in FIG. 2, a portion of the blood will flow into each blood unit.

The flow of water and oxygen are opposite to the flow of blood in the sense that they enter through end plate 11b and leave through end plate 11a, whereas blood enters through end plate 11a and leaves through end plate 11b, but within the respective water and oxygen units 26 and 27 the flow is as shown in FIG. 2, a portion of the flow of each fluid being diverted at the level of each respective water or oxygen unit for flow through that unit. It will be seen that the flow of blood and the flow of water are upwards. Thus at the level of each blood unit 28 that portion of the stream of blood which is diverted into such unit flows upwards into the blood space 33a, and at the level of each water unit 26 that portion of the stream of water which is diverted into such unit also flows in an upward direction. This aids in avoiding entrapment of air or other gas which is especially important in the case of the blood because such entrapment could cause an embolism.

In start up (after the water and blood units 26 and 28 are tested and the completely assembled apparatus is tested as described below) the apparatus is primed and in priming care is taken to remove all air or other gas from the blood and water circuits. This is aided by the upward flow patterns noted above and shown in FIG. 2 and it is also aided by tilting the apparatus (see FIG. 1) so that the lower edge of end plate 11a is lower than the lower edge of end plate 11b and so that the right-hand ends (as viewed in FIG. 1) of the end plates are higher than their other ends. Therefore, the blood flow at all times has an upward component. Therefore when the apparatus is primed and ready for use, it is free of entrapped gas, and it remains free of gas during use. This is, as noted, especially important in the case of the blood circuit. The apparatus is held, by suspension or otherwise, in the doubly tilted attitude (i.e., tilted about one edge and about one end) during use.

In the claims or elsewhere where reference is made to "horizontal", "vertical", "above", "below" or where words of like import are used to describe the spatial arrangement of components, such is with reference to the apparatus as shown in FIGS. 4 and 6 wherein the end plates 11a and 11b are assumed to be horizontal. As will be apparent, when the apparatus is in use it is preferably in a tilted position as described above.

As noted above, the end plates 11a and 11b are shown in FIGS. 1 and 2 as rectangular prisms, but their preferred construction is otherwise. A suitable construction is shown by way of example in FIGS. 6 and 7. As will be seen from FIG. 6, each of the end plates comprises a solid plate 90 of suitable material, for example polycarbonate, acrylic resin or acrylonitrile-butadiene-styrene resin. This plate is reinforced by longitudinal ribs 91 and lateral ribs 92. The entire construction may be molded in one piece. Bolt holes are shown at 93 to receive the bolts 13. Referring now particularly to FIG. 7, it will be seen that outer edge 94 is chamfered, the angle of the chamfer being typically about 1°.

The chamfer surfaces 94 intersect the major, interior flat surface of the plate along fulcrum lines 94a which are located inwardly not only of the bolt holes 93 but also of the flow-through slots 43 and 48 (see FIG. 8) and the blood flow grooves or manifolds (see FIG. 2). Therefore, as the bolts 13 are tightened the chamfered edges 94 (which extend around the entire periphery of the end plates) are pulled toward one another with the intersection of the chamfers and the flat central portions of the end plates acting as fulcrums. When the water mattresses are filled with water under pressure, typically about 12 psi gauge, the water pressure also tends to force the chamfered edges of one plate toward those of the other plate. These forces in turn act on the edge portions of the stack 12 of blood, water and oxygen units, thereby ensuring more nearly uniform pressure intensity between the joint making contact surfaces in the periphery of the stack. This feature and a variant are further described below with reference to FIGS. 21 and 22.

In assembling and testing the components of the apparatus described hereinabove and illustrated in the drawings, the following procedure is recommended:

Each blood unit 28 is tested separately and each water unit 26 is tested separately before assembling. Each blood unit is tested by clamping it in a testing device comprising plates similar to the end plates 11a and 11b, filling it with distilled water, and observing whether water leaks, either by observation of pressure change or by observation of drop in a column of water in a transparent tube extending up from the outlet.

The water unit may be tested similarly but more conveniently by filling it with air under pressure and observing a pressure gauge to determine holding or loss of pressure.

Then the blood and water units are assembled including spacers as shown at 50 and 65 in FIGS. 8, oxygen screens as shown in FIG. 8, and inserts as shown at 47 in FIG. 5, also end plates 11a and 11b as shown in FIG. 6 and bolts 13 are applied and their nuts are tightened. A room temperature vulcanizing adhesive is applied to the spaces 100 between the spacers 50 and the stack of water and oxygen units 26 and 27. There are four such spaces, one at each corner, two such spaces being shown at 100 in FIG. 3, the cured or vulcanized adhesive being shown at 101. Then the assembly of blood, oxygen and water circuits is tested as follows:

The water circuit is filled with compressed air and a pressure gauge is employed to determine whether there is a drop in pressure. Then the blood circuit is tested by filling it with distilled water while maintaining air pressure in the water circuit. Any outward leakage from the blood circuit is visibly evident. A leak from the interior of the blood circuit, e.g., from one of the blood envelopes, is made evident by the presence of water in the oxygen circuit which remains open and will leak water through its outlet.

All parts of the oxygenator to be in contact with any of the circulating fluids (blood, water and oxygen) are sterilized, for example, by known ethylene oxide sterilization procedures.

In use, the assembled apparatus is connected as shown in FIG. 1 and as described above, to water and oxygen supplies and to the venous and arterial systems of the patient and to other necessary equipment.

In the description above and in FIGS. 3, 5 and 13 the semi-permeable membranes 33 are shown as being heat sealed at 46 to the side members 31 of blood frame 30. Difficulty may be encountered at the junctions of the heat seals along the side members 31 and the end members 32, such as wrinkles in the membrane in the adjacent area. This may be remedied by relying upon pressure seals along the side members rather than heat seals, leaving heat seals only along the end members 32. The chamfers 94 (see FIG. 7) and the advantages conferred by them as described above allow such pressure seals to be used if such are deemed advisable.

Dimensions of the apparatus are of importance in the light of requirements of a patient. Following criteria and recommendations will be of help in the practice of the invention:

The blood circulation of the average adult person at rest is about 5 liters of blood per minute, and the patient will require about 200 cc of oxygen per minute at atmospheric pressure and body temperature (98.6° F.). It has been found that these requirements are met by apparatus having approximately twelve blood units each 7½ inches from blood inlet to outlet side, and 18 inches in width of blood paths. More precisely, these dimensions are 7½ inches from the outlet ends of the slots 44 (or grooves 82 in FIG. 13) to the inlet ends of the corresponding slots or grooves in the opposite side member, and 18 inches from the inner edge of one end of member 32 to the inner edge of the other end member 32. The thickness of the blood screen, which determines the thickness of the blood space 33a and hence the thickness of the blood path, is preferably about 0.020 inch. Typical dimensions of the water and oxygen units are 23 inches by 7½ inches. The oxygen screen 68 and the blood screen 34 promote uniform flow of the respective fluids. Moreover, the blood screen 34 provides a gently turbulent flow of blood which does not harm the blood yet promotes efficient contact with the oxygen that diffuses through the membranes 33 and efficient transfer of carbon dioxide from the blood units to the oxygen units.

There may, of course, be departures from these dimensions. The length of the blood path in each blood unit, that is, the distance between the inner edges of the side members 31 of the blood frame, may be increased thereby allowing more oxygen to be absorbed by the blood in its transit through a blood unit, and also a correspondingly greater diffusion of carbon dioxide from the blood into the oxygen stream. However, longer blood paths present more resistance to flow, so that greater pressures will be required.

The length of each blood unit may depart from the 18 inch figure described above; thus more than 12 units may be used, each having a shorter dimension than 18 inches, or this dimension may be increased and fewer units employed. In the latter case, if the departure is considerable, the size of the components may introduce manufacturing difficulties, and the device may be somewhat cumbersome.

It has been found that a flow rate designed to effect about 95% saturation of the blood with oxygen is satisfactory. Since oxygen is relatively inexpensive and is vented from the system, high oxygen flow rates are favored, such as seven liters per minute per square meter of effective membrane area.

Among advantages of the apparatus described and illustrated above are the following: The components may be made of readily available and relatively inexpensive plastic material by economical methods, such as molding and/or stamping. The overall dimensions are typically about 23 inches in length, 10 inches in width, and 4 inches in height (a total volume of 920 cubic inches) which is a convenient size for use in an operating facility. (Length is the long dimension in FIG. 1, width is the distance between the outer surfaces of the end plates and height is the distance between the upper and lower edges of the end plates in FIG. 1.)

The apparatus can be manufactured at a cost such that it is disposable and may be used once and discarded.

The water and blood circuits operate at pressures higher than the pressure in the oxygen circuit, and the water and blood circuits are so designed that any leakage from the water circuit will be either to the exterior of the apparatus or into the oxygen space. Therefore, leakage of water into the blood circuit is precluded.

The chamfer 94 described above with reference to FIG. 7 ensures a tight, even application of pressure. Reference is now made to FIG. 21 which also shows one of two gaskets 95 of compressible material such as rubber which are placed only on those long sides where there are no blood manifolds 17 in the end plates 11a and 11b. To prevent contact of rubber with blood, these gaskets are covered with a blood-compatible plastic polyethylene on the side facing the stack. As bolt pressure is applied the tapered edges of the cover plates bend about the fulcrum lines 94a where the plane of the chamfer 94 meets the plane of the flat major interior surfaces of the end plates. This causes the central portion of the end plates to bend outwardly. When the apparatus is in operation with water flowing through the water mattresses at, for example, 12 psi gauge pressure, the water pressure combined with the tension in the bolts causes additional outward bending of the central portion of the end plates. It will be understood that such a bending is very small in magnitude but is sufficient to reduce the pressure intensity along the inside seal line. If the elasticity of the compressed stack is low, leakage of blood into the oxygen space may result. This elasticity is ensured by the presence of the gasket 95 to prevent leaks. The directions of the forces involved are shown in FIG. 21 by the arrows.

Referring now to FIG. 22, which is similar to FIG. 7, the use of a tapered wedge 96 is shown which provides the chamfer 94. An advantage of this construction is that tapered wedges may be less expensive to manufacture than chamfered end plates. Another advantage is that if different chamfers are required for different materials of construction of the stack 12 and/or for different sizes of stacks, the end plates may be uniform but fitted with appropriate wedges.

Referring now to FIGS. 14 and 20, an alternative form of water unit is there shown and is designated generally by the reference numeral 26a. It comprises a water mattress or bladder 110 formed of water-impermeable, gas-impermeable, flexible material as in the case of the bladder or mattress 52 shown in FIG. 8 and described hereinabove. This mattress is fitted at one end (the right-hand end as viewed in FIG. 14) with two inserts 111, each formed with a water flow-through slot 112 and with lateral passages or grooves 113. At its other end the bladder is fitted with an oxygen insert 114, which is of solid construction and is formed with two oxygen flow-through slots 115. Side members (not shown) such as those shown at 50 in FIG. 8 will be employed.

The construction of the water insert 111 may be as shown in FIG. 8, that is to say, it may be formed of three pieces, or it may have, and preferably it does have, the simpler two-piece construction shown in FIG. 9. The water mattress 110 is sealed at 116 from one end (the right end or water end) to a point short of the oxygen insert, thereby leaving a space or channel 117.

In operation with this type of water unit, oxygen flows through the slots 115 in the oxygen insert 114 without access to the interior of the water bladder. Meanwhile water flows in through the slot 112 in one of the inserts 111 and a portion of the water flows through the lateral passages 113 into the interior of the water mattress on one side of the seal 116, then through the space 117 to the other side and out through lateral passages 113 and slot 112.

An advantage of this type of construction is that it minimizes the extent of stagnant areas of water.

Referring now to FIGS. 15 to 19, an alternative form of oxygen unit is there shown which is generally designated by the reference numeral 120. It comprises a screen 121 which, except in the respects mentioned immediately below, is identical with the screen 68 shown in FIG. 8. The screen 120 is slotted at 122 and is punched with holes 123.

At one end the screen 121 butts against a water flow-through insert 124 having slots 125 which register with the slots 112 of the water units. At its other end the oxygen unit is provided with an oxygen distributor or insert 125A which is formed with oxygen flow-through slots 126 and lateral passages 127. As will be seen in FIG. 17, the inner edge of the insert 125A is bifurcated to receive the adjacent end of the screen 121. Further, the oxygen insert 125A is of two-piece construction as shown in FIG. 18, and the bottom piece is provided with pegs 128 which extend through holes 123 in the screen 121 and into holes 130 in the top piece.

As will be further seen, a T-member 135 is provided the leg of which fits into the slot 122 in the screen 121 and is also received in a notch 136 in the insert 125A to lock the screen 121 and the insert 125A together. This oxygen unit will be provided with side pieces 50 as shown in FIG. 8.

In operation, water flows through the passages 125 without access to the interior of the oxygen unit and oxygen flows through one of the slots 126 and a portion of the oxygen flows through the lateral passages 127 into the interior of the oxygen unit on one side of the T, then around through the space 137 at the end of the T and through the passages 127 into the other slot 126 and thence to the next level.

The blood oxygenator described above employs a gas-permeable, water-impermeable member through which only gases flow. However, the apparatus of the invention is applicable to a more recent type of oxygenator which employs an aqueous solution of hydrogen peroxide as the source of the oxygen gas. This type of oxygenator employs a semi-permeable membrane through which water as well as gas may flow and through which small solute molecules such as inorganic salts may also pass. The membrane is provided with a catalyst that acts to break down the hydrogen peroxide diffusing through it into water and oxygen. The hydrogen peroxide solution also contains salts to maintain a suitable osmotic pressure, such salts being compatible with the blood of the patient. This type of oxygenator is described in U.S. Pat. Nos. 3,846,236 and 3,996,141 and in papers by the patentee, Stuart Updike, in Transactions of the American Society of Artificial Internal Organs, Vol. 19, page 529, and Vol. 20, page 286.

In applying the present invention to this type of oxygenator, the only changes (other than size, which could be smaller with the hydrogen peroxide system) would be to use an appropriate semi-permeable membrane which is permeable to gas, water and small solute molecules but impermeable to the formed elements of the blood such as red and white blood cells, platelets etc., and to proteins carried by the blood, etc. The membrane would also embody a catalyst. Further, the oxygen circuit and its components would be used with aqueous hydrogen peroxide solution rather than gaseous oxygen.

It will therefore be apparent that a new and advantageous oxygenator of the membrane type and new and useful components of such an oxygenator have been provided.

I claim:

1. A blood unit adapted for use in a blood oxygenator of the type wherein there is a stack of blood units, oxygen units and water units with each blood unit separated from the nearest water unit or units by at least one oxygen unit, and wherein the water units are of the expansible type which, when filled with water under pressure, exert pressure on neighboring blood units, such pressure being transmitted through the intervening oxygen units, said blood unit comprising:
   (a) a frame having opposing sides and opposing ends enclosing an open space,
   (b) blood flow-through passage means being formed on the sides for flow of blood through the blood unit from one face to the other face of the unit,
   (c) lateral passages communicating such flow-through passage means with the open space of the frame for diverting a portion of the flow of blood from the flow-through passage means on one side of the frame into the open space of the frame, through such space into the flow-through passage means on the other side of the frame and then out of the blood unit,
   (d) the ends of the frame adjacent the open space of the frame being imperforate,
   (e) semipermeable membrane means which is permeable to gas but impermeable to water covering the open space of the frame to provide with the inner edges of the frame, a blood space enclosed by the membrane means and such inner edges, and accessible to such laterial passages,
   (f) said frame being provided at each end with water flow-through passage means and oxygen flow-through passage means for flow of water and flow of oxygen, respectively, from above to below the level of the blood unit, such flow-through means being isolated from the blood space, each end of the frame being formed between the water flow-through passage means and at least one side of the frame with a gap, including a leak passage, through which water leaking from the water flow-through passage means may leak to the level of an adjacent oxygen unit.

2. The blood unit of claim 1 wherein the water flow-through passage means is formed in a separate piece spaced from the respective end of the frame.

3. The blood unit of claim 1 wherein said blood space is provided with a screen which acts to distribute blood evenly, to provide efficient diffusion of oxygen into the blood and of carbon dioxide out of the blood, and to define the thickness of the blood path in said cavity.

* * * * *